United States Patent
Kim et al.

(10) Patent No.: US 11,647,358 B2
(45) Date of Patent: May 9, 2023

(54) METHOD FOR OBTAINING LOCATION INFORMATION OF A USER USING MOVEMENT INFORMATION OF AN ELECTRONIC DEVICE OR FEATURE INFORMATION

(71) Applicant: Samsung Electronics Co., Ltd., Suwon-si (KR)

(72) Inventors: Jaehong Kim, Suwon-si (KR); Heungryong Oh, Suwon-si (KR); Keuncheol Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 194 days.

(21) Appl. No.: 17/171,550

(22) Filed: Feb. 9, 2021

(65) Prior Publication Data

US 2022/0030388 A1 Jan. 27, 2022

(30) Foreign Application Priority Data

Jul. 24, 2020 (KR) .................. 10-2020-0092329

(51) Int. Cl.
*H04W 4/00* (2018.01)
*H04W 4/02* (2018.01)
(Continued)

(52) U.S. Cl.
CPC ............. *H04W 4/027* (2013.01); *G06N 3/04* (2013.01); *G06N 3/08* (2013.01); *H04W 4/029* (2018.02); *A61B 5/6898* (2013.01)

(58) Field of Classification Search
CPC ........ H04W 4/027; H04W 4/029; G06N 3/04; G06N 3/0445; G06N 3/0472; G06N 3/08; A61B 5/6898
See application file for complete search history.

(56) References Cited

U.S. PATENT DOCUMENTS 8,934,884 B2 1/2015 Gustafsson et al.
10,209,779 B2 2/2019 Roh et al.
(Continued)

FOREIGN PATENT DOCUMENTS

KR 10-2015-0099430 A 8/2015
KR 10-2017-0105827 A 9/2017
(Continued)

OTHER PUBLICATIONS

International Search Report dated Apr. 15, 2021, issued in International Application No. PCT/KR2020/016663.

*Primary Examiner* — Pakee Fang
(74) *Attorney, Agent, or Firm* — Jefferson IP Law, LLP

(57) ABSTRACT

An electronic device and a method for controlling the same are provided. The electronic device includes a communicator including circuitry, a first sensor configured to detect movement information of the electronic device, a memory including a first determination module configured to determine whether a user carries the electronic device and a second determination module configured to determine a detecting method for detecting a user location, and a processor configured to identify whether a user of the electronic device carries the electronic device based on the movement information of the electronic device obtained by the first sensor by using the first determination module, and determine a detecting method for detecting location information of the user according to whether the user carries the electronic device by using the second determination module.

20 Claims, 9 Drawing Sheets

(51) Int. Cl.
*H04W 4/029* (2018.01)
*G06N 3/08* (2023.01)
*G06N 3/04* (2023.01)
*A61B 5/00* (2006.01)

(56) References Cited

U.S. PATENT DOCUMENTS

| | | |
|---|---|---|
| 10,270,642 B2 | 4/2019 | Zhang et al. |
| 10,463,914 B2 * | 11/2019 | Seo .................. G06F 3/016 |
| 10,534,900 B2 | 1/2020 | Cheong et al. |
| 10,897,687 B2 | 1/2021 | Kwon et al. |
| 10,921,438 B2 | 2/2021 | Jeon et al. |
| 11,435,187 B2 | 9/2022 | Kim et al. |
| 2013/0311084 A1 * | 11/2013 | Lundquist ............ G01C 21/206 |
| | | 701/410 |
| 2014/0087707 A1 | 3/2014 | Gustafsson et al. |
| 2016/0006266 A1 | 1/2016 | Park et al. |
| 2017/0010677 A1 * | 1/2017 | Roh ..................... G06F 3/1454 |
| 2017/0011210 A1 | 1/2017 | Cheong et al. |
| 2017/0171712 A1 * | 6/2017 | Luo ..................... H04W 4/023 |
| 2019/0072661 A1 | 3/2019 | Jeon et al. |
| 2019/0187802 A1 | 6/2019 | Roh et al. |
| 2020/0033130 A1 | 1/2020 | Kim et al. |
| 2020/0084574 A1 | 3/2020 | Kwon et al. |

FOREIGN PATENT DOCUMENTS

| | | |
|---|---|---|
| KR | 10-1808095 B1 | 12/2017 |
| KR | 10-2019-9030022 A | 3/2019 |
| KR | 10-2064680 B1 | 1/2020 |
| KR | 10-2020-0011209 A | 2/2020 |
| KR | 10-2073696 B1 | 2/2020 |
| KR | 10-2020-0029271 A | 3/2020 |

\* cited by examiner

METHOD FOR OBTAINING LOCATION INFORMATION OF A USER USING MOVEMENT INFORMATION OF AN ELECTRONIC DEVICE OR FEATURE INFORMATION

CROSS-REFERENCE TO RELATED APPLICATION(S)

This application is based on and claims priority under 35 U.S.C. § 119(a) of a Korean patent application number 10-2020-0092329, filed on Jul. 24, 2020, in the Korean Intellectual Property Office, the disclosure of which is incorporated by reference herein in its entirety.

BACKGROUND

1. Field

The disclosure relates to an electronic device and a method for controlling the electronic device. More particularly, the disclosure relates to an electronic device which determines a user detecting method based on whether a user carries the electronic device and a method for controlling the same.

2. Description of Related Art

A user may identify a location of a user terminal device carried by the user by using a location-based service. The location-based service may refer to a system for providing various services to users based on location information obtained via a mobile communication network or a global positioning system.

However, in a case of the location-based service with the global positioning system, it is difficult to use indoors. Accordingly, in the related art, a location determination technology for identifying a location of a user terminal device using a network system, such as a communication module included in the user terminal device or a wireless-fidelity (Wi-Fi) system installed in the surrounding environment has been developed and used.

Meanwhile, the user does not carry the user terminal device all the time and may act while placing the user terminal device at a specific location. When the user acts without carrying the user terminal device, a location of the user is different from a location of the user terminal device. In a case of using the location determination technology designed assuming the situation that the user carries the terminal device, there is a limit of output of user position estimation (or localization) information with deteriorated accuracy.

The above information is presented as background information only to assist with an understanding of the disclosure. No determination has been made, and no assertion is made, as to whether any of the above might be applicable as prior art with regard to the disclosure.

SUMMARY

Additional aspects will be set forth in part in the description which follows and, in part, will be apparent from the description, or may be learned by practice of the presented embodiments.

In accordance with an aspect of the disclosure, an electronic device is provided. The electronic device includes a communicator including circuitry, a first sensor configured to detect movement information of the electronic device, a memory including a first determination module configured to determine whether a user carries the electronic device and a second determination module configured to determine a detecting method for detecting a user location, and a processor configured to identify whether a user of the electronic device carries the electronic device based on the movement information of the electronic device obtained by the first sensor by using the first determination module, and determine a detecting method for detecting location information of the user according to whether the user carries the electronic device by using the second determination module, in which the processor is configured to, based on the user being identified to carry the electronic device, determine a first detecting method for obtaining the location information of the user using at least one of the movement information of the electronic device or feature information of a first signal received from an access point (AP) via the communicator, and based on the user being identified to not carry the electronic device, determine a second detecting method for obtaining the location information of the user using feature information of a second signal received from at least one external device via the communicator.

In accordance with another aspect of the disclosure, a method for controlling an electronic device including a first sensor configured to detect movement information of the electronic device, a first determination module configured to determine whether a user carries the electronic device, and a second determination module configured to determine a detecting method for detecting a user location is provided. The method includes identifying whether a user of the electronic device carries the electronic device based on the movement information of the electronic device obtained by the first sensor by using the first determination module, and determining a detecting method for detecting location information of the user according to whether the user carries the electronic device by using the second determination module, in which the determining includes, based on the user being identified to carry the electronic device, determining a first detecting method for obtaining the location information of the user using at least one of the movement information of the electronic device or feature information of a first signal received from an AP, and based on the user being identified to not carry the electronic device, determining a second detecting method for obtaining the location information of the user using feature information of a second signal received from at least one external device Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

An aspect of the disclosure is to provide an electronic device which identifies whether a user carries the electronic device and determines a method for detecting a location of the user based on the identified result, and a method for controlling the same.

Hereinafter, various embodiments of the disclosure will be described with reference to the drawings.

Figure 1:
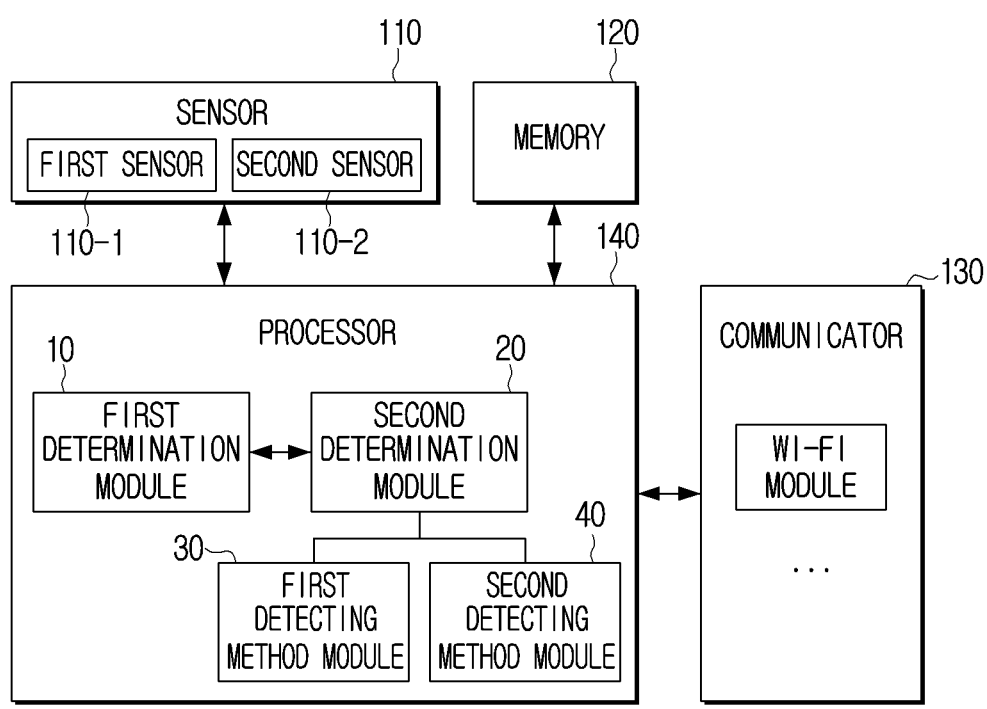
FIG. 1 is a block diagram for illustrating a configuration and an operation of an electronic device according to an embodiment of the disclosure.

FIG. 1 is a block diagram for illustrating a configuration and an operation of an electronic device according to an embodiment of the disclosure.

Referring to FIG. 1, an electronic device 100 may include a sensor 110, a memory 120, a communicator 130, and a processor 140.

The configuration illustrated in FIG. 1 is a diagram for implementing the embodiments of the disclosure and appropriate hardware and software configurations apparent to those skilled in the art may be additionally included in the electronic device 100.

In describing the disclosure, the electronic device 100 may be implemented as a user terminal device, such as a smartphone, a tablet personal computer (PC), a laptop PC, a notebook computer, a medical device, and a wearable device, but is not limited thereto.

The sensor 110 may detect various state information of the electronic device 100 or state information of a user carrying (or wearing) the electronic device 100. The sensor 110 may include a first sensor 110-1 for detecting movement information of the electronic device 100 and a second sensor 110-2 for detecting information regarding a user carrying or wearing the electronic device 100.

The first sensor 110-1 may include at least one of a gyro sensor, an acceleration sensor, and a geomagnetism sensor. The gyro sensor may detect information regarding angular velocity of the electronic device 100.

The information regarding the angular velocity obtained via the gyro sensor may be used to identify a degree of a tilt of the electronic device 100 or rotation of the electronic device 100. The geomagnetism sensor is a sensor for detecting magnetism and information obtained via the geomagnetism sensor may be used to obtain information regarding an azimuth of the electronic device 100.

The acceleration sensor may detect information regarding dynamic forces of the electronic device 100, such as an acceleration, vibration, impact, and the like. The information regarding dynamic forces obtained via the acceleration sensor may be used to identify information of a force applied to the electronic device 100 or steps of a person carrying the electronic device 100. Herein, the operation information may include information regarding whether the user is walking with the electronic device 100 and the number of times of steps.

The second sensor 110-2 may include a sensor for detecting a biological signal of the user (e.g., a blood pressure sensor, a blood glucose sensor, a heart rate sensor, and the like). The sensor for detecting the biological signal of the user may detect various biological signals, such as blood pressure, heart rate, and the like by coming into contact with or being spaced apart, within a preset distance, from a body of the user carrying or wearing the electronic device 100.

For example, if the electronic device 100 is implemented as a wearable device, the second sensor 110-2 may detect various biological signals, such as blood pressure, blood rate, and the like of the user wearing the electronic device 100. If the user takes off the electronic device 100, the second sensor 110-2 may not come into contact with or may not be spaced apart, within a preset distance, from the body of the user. At that time, the second sensor 110-2 may not detect the biological signal of the user of the electronic device 100.

In addition to the first sensor 110-1 and the second sensor 110-2, the sensor 110 may further include a sensor for detecting location information (e.g., a global positioning system (GPS) sensor), a sensor for detecting environment information around the electronic device 100 (e.g., a temperature sensor, a humidity sensor, a pressure sensor, and the like), a sensor for detecting presence of the user (e.g., a camera, a UWB sensor, an IR sensor, a proximity sensor, an optical sensor, and the like), and the like.

The memory 120 may store an instruction or data related to at least another element of the electronic device 100. The memory 120 may be accessed by the processor 140 and reading, recording, editing, deleting, or updating of the data by the processor 140 may be executed.

A term, memory, in the disclosure may include the memory 120, a ROM (not illustrated) and RAM (not illustrated) in the processor 140, or a memory card (not illustrated) (e.g., micro SD card or memory stick) mounted on the electronic device 100. In addition, the memory 120 may store programs and data for configuring various screens to be displayed in a display area of a display.

The memory 120 may store an instruction set corresponding to at least one program executable by the processor 140. The instruction may refer to one action statement executable directly by the processor 140 in a programming language and is a minimum unit of execution or an action of a program.

The memory 120 may store a first determination module for determining whether the user carries the electronic device 100 and a second determination module for determining a user location detecting method. The first determination module and the second determination module may be implemented as software modules and controlled by the processor 140. However, this is merely an embodiment of the disclosure, and each determination module may be implemented as a separate hardware module controlled by the processor 140.

A first determination module 10 may be a module for determining whether the user carries the electronic device 100 by using movement information of the electronic device 100 or a biological signal of the user of the electronic device 100. The user carrying the electronic device 100 may imply that the user carries, wears, or uses the electronic device 100.

A second determination module 20 may be a module for determining a detecting method for detecting a user location based on whether the user carries the electronic device 100 or whether the battery of the electronic device 100 is being charged.

The memory 120 may store a plurality of detecting method modules (e.g., a first detecting method module 30 and a second detecting method module 40). When the method for detecting the user location is determined by the second determination module 20, the detecting method module corresponding to the determined detecting method among the plurality of detecting method modules may perform operations to obtain location information of the user. The operations and functions of each detecting method module may be controlled by the processor 140. The operation that the processor 140 controls each module to obtain the location information of the user will be described later.

Meanwhile, in describing the disclosure, the location information of the user may include, not only information regarding an area where the user is located, but also information related to whether the user is present within a threshold distance from the electronic device or an external device.

The memory 120 may store a plurality of location detecting models (e.g., a first location detecting model, a second location detecting model, and a third location detecting model).

The first location detecting model may be an artificial intelligence model trained using a fingerprint database as learning data. The first location detecting model may be trained to, when feature information of a first signal is input, identify a fingerprint matched with the feature information of the first signal from the fingerprint database, and output location information of the user corresponding to the identified fingerprint.

The first signal may refer to a Wi-Fi signal received via a Wi-Fi network. The feature information of the first signal may include at least one of channel state information (CSI), time of arrival (TOA), an angle of arrival (AOA), and a received signal strength (RSS) of the first signal.

The fingerprint may refer to data including the feature information of a signal (e.g., Wi-Fi signal) receivable from an access point (AC), when the electronic device 100 is located at a specific location. The feature information of the signal receivable by the electronic device 100 from the AP varies depending on the location, the fingerprint may be classified according to the location. The AP may refer to a device which enables wireless devices to connect to a wired network using Wi-Fi-related standard.

The fingerprint database may be a database in which a plurality of fingerprints classified for each location are stored and structured. The fingerprint database may also be expressed as radio map information.

The second location detecting model may be an artificial intelligence model trained to output current location information of the user based on a plurality of predefined locations of the electronic device based on feature information of a second signal. Herein, the second signal may refer to a Wi-Fi signal received via the Wi-Fi network and the type of the feature information of the second signal may be the same as the type of the feature information of the first signal. The predefined location of the electronic device may refer to a location learned by the second location detecting model.

The second location detecting model may be trained using the feature information of the second signal received from an external device at the predefined location of the electronic device 100 and the current location information of the user as the learning data.

As the location of the electronic device 100 changes, the feature information of the second signal receivable by the electronic device 100 from other external devices may change. The second location detecting model may be trained using the learning data described above at a plurality of predefined locations determined from the user.

The third location detecting model may be an artificial intelligence model trained to output location information of the electronic device based on feature information of a signal. The third location detecting model may be trained using feature information of a signal received from at least one external device and current location information of the electronic device matched with each feature information as the learning data.

The memory 120 may include a non-volatile memory holding stored information, even if the power supply is interrupted, and a volatile memory that needs continuous power supply to hold the stored information. Referring to FIG. 1, the volatile memory may be implemented in a form included in the processor 140 as an element of the processor 140, but this is merely an embodiment of the disclosure, and the volatile memory may be implemented as an element separated from the processor 140.

The communicator 130 may include circuitry and communicate with the AP or an external device. The communicator 130 may include various wireless communication modules and the wireless communication module may include a Wi-Fi module 130-1.

The Wi-Fi module 130-1 may receive a Wi-Fi signal from the AP or various external devices. The Wi-Fi module 130-1 may measure feature information of the Wi-Fi signal while receiving the Wi-Fi signal. For example, the Wi-Fi module 130-1 may obtain channel state information, time of arrival, an angle of arrival, phase information, signal strength, and the like of the received Wi-Fi signal.

In describing the disclosure, the external device may include at least one of a smartphone, a tablet PC, a desktop PC, a laptop PC, a netbook PC, a server, a PDA, a medical device, or a wearable device. In some embodiments of the disclosure, the external device may include at least one of, for example, a television, a refrigerator, an air conditioner, an air purifier, a set-top box, a media box (e.g., SAMSUNG HOMESYNC™). However, there is no limitation to the above examples and the external device may be implemented as various types of devices.

The processor 140 may be electrically connected to the memory 120 to control general functions and operations of the electronic device 100. The processor 140 may load the plurality of determination modules 10 and 20 and the detecting method modules 30 and 40 from the non-volatile memory to the volatile memory. The loading may refer to an operation of invoking data stored in the non-volatile memory to the volatile memory to store the data so that it is accessible by the processor 140.

In an embodiment of the disclosure, when the power of the electronic device 100 is turned on, the processor 140 may load each determination module and detecting method module to the volatile memory. In another embodiment of the disclosure, when a command for activating a user location detecting function is input from the user, the processor 140 may load each determination module and the detecting method module to the volatile memory.

The processor 140 may identify whether the user carries the electronic device based on movement information of the electronic device 100 obtained via the first sensor 110-1 using the first determination module 10.

In an embodiment of the disclosure, when the movement information (e.g., a tilt value, a rotation angle, or the like of the electronic device 100) obtained via the first sensor 110-1 is changed within a first threshold time, the processor 140 may identify that the user carries the electronic device via the first determination module 10.

In another embodiment of the disclosure, when the movement information is changed by a preset value or more within the first threshold time, the processor 140 may identify that the user carries the electronic device via the first determination module 10. Herein, the preset value may be changed by the user.

For example, when the electronic device 100 rotates from a vertical direction (portrait direction) to a horizontal direction (landscape direction) by the user, the processor 140 may identify that the rotation angle of the electronic device 100 is changed via the first sensor 110-1. The change of the rotation angle of the electronic device 100 may imply that the user carries and uses the electronic device 100. Since the rotation angle of the electronic device 100 is changed within the first threshold time, the processor 140 may identify that the user carries the electronic device using the first determination module.

When the movement information obtained via the first sensor 110-1 is not changed within the first threshold time, the processor 140 may identify that the user does not carry the electronic device via the first determination module 10. The first threshold time may be preset time but may be changed by the user.

The processor 140 may identify whether the user carries the electronic device 100 based on whether the biological signal of the user is able to be detected via the second sensor 110-2 by using the first determination module 10. The processor 140 may obtain the biological signal of the user via the second sensor 110-2 coming into contact with or spaced apart, within a preset distance, from the user of the electronic device 100.

If the biological signal of the user is not obtained within a second threshold time via the second sensor 110-2, the processor 140 may identify that the user does not carry the electronic device 100 via the first determination module 10. When the biological signal of the user is obtained within the second threshold time via the second sensor 110-2, the processor 140 may identify that the user carries the electronic device 100 via the first determination module 10.

When it is identified whether the user carries the electronic device via the first determination module 10, the processor 140 may determine the detecting method for detecting the location information of the user based on the identified result by using the second determination module 20.

When it is identified that the user carries the electronic device 100, the processor 140 may determine a first detecting method (or device-carry detecting method) for obtaining the location information of the user by using at least one of the movement information of the electronic device and the feature information of the first signal received from the AP via the communicator 13.

When the first detecting method is determined, the processor 140 may obtain the location information of the user using the first detecting method module 30 corresponding to the determined first detecting method among the plurality of detecting method modules.

In an embodiment of the disclosure, the processor 140 may obtain the location information of the user by using dead reckoning based on the movement information of the electronic device 100 from the first detecting method via the first detecting method module 30. The dead reckoning may be a method for estimating a current location of an electronic device based on a direction and a distance the electronic device is moved by the user from a reference location.

Specifically, the processor 140 may obtain operation information via the acceleration sensor and may obtain information regarding a direction of the electronic device is moved by the user via the gyro sensor or the geomagnetism sensor. The processor 140 may estimate a direction and a distance the electronic device is moved from the reference location by using the movement information of the electronic device 100 via the first detecting method module 30. Herein, the reference location may be a fixed location where the electronic device is not moved by the user within preset time or a location set as the reference location by the user.

Accordingly, the processor 140 may obtain the current location information of the electronic device 100 moved from the reference location by using the first detecting method module 30. Since it is identified that the user carries the electronic device 100, the location information of the electronic device 100 may refer to location information of the user.

In another embodiment of the disclosure, the processor 140 may obtain the location information of the user using a fingerprint comparing method from the first detecting method via the first detecting method module 30. The fingerprint comparing method is a method for identifying a fingerprint matched with the feature information of the signal received from the AP among fingerprints included in the fingerprint database stored in advance and estimating current location information of the electronic device using location information included in the identified fingerprint.

The processor 140 may obtain the location information of the user using the fingerprint comparing method based on the feature information of the first signal obtained via the communicator 130 using the first detecting method module 30. Specifically, the processor 140 may identify the fingerprint matched with the feature information of the first signal by inputting the feature information of the first signal to the first location detecting model and obtain the location information of the user corresponding to the identified fingerprint via the first detecting method module 30.

When it is identified that the user does not carry the electronic device 100, the processor 140 may determine a second detecting method (or a device-free detecting method) for obtaining the location information of the user using the feature information of the second signal received from at least one external device via the second determination module 20. The processor 140 may obtain the location information of the user by using the second detecting method module 40 corresponding to the determined second detecting method among the plurality of detecting method modules.

The processor 140 may control the communicator 130 to transmit a signal requesting transmission of the second signal for obtaining the location information of the user to the external device via the second detecting method module 40. When the request signal is received, the external device may emit the second signal via various paths. The processor 140 may receive the entirety or a part of the second signal emitted from the external device via the communicator 130.

Meanwhile, a part or the entirety of the second signal emitted from the external device may be reflected by or transmitted through the user to be transmitted to the electronic device 100. Feature information of the second signal received by being reflected by or transmitted through the user may be different from the feature information of the signal transmitted to the electronic device 100 directly from the external device.

The processor 140 may receive a part or the entirety of the second signal emitted from the external device via the communicator 130 and obtain the feature information of a part or the entirety of the second signal. For example, the processor 140 may receive the entirety or a part of a Wi-Fi signal emitted from the external device and obtain CSI, RSS, AOA, or TOA of each of the entirety or a part of the received Wi-Fi signal. A part or the entirety of the Wi-Fi signal received via the communicator 130 may be a signal reflected by or transmitted through the user.

The processor 140 may obtain the location information of the user by inputting the feature information of the second signal to the second location detecting model via the second detecting method module 40. The second location detecting model has been trained to output the location information of the user based on the predefined location that is learned. Accordingly, when the processor 140 inputs the feature information of the second signal to the second location detecting model, the location of the electronic device 100 may be a predefined location learned by the second location detecting model.

For example, when a CSI magnitude change amount of the Wi-Fi signal received from the external device via a first path and a second path is input to the second location detecting model, the processor 140 may obtain the location information of the user for measuring the location of the user based on the current location of the electronic device 100 via the second detecting method module 40.

The processor 140 may identify whether the user is present within a threshold distance of the electronic device 100 based on the obtained location information of the user. The location information of the user may include information regarding whether the user is present within the threshold distance of the electronic device 100.

When it is identified that the user is present within the threshold distance of the electronic device based on the obtained location information of the user, the processor 140 may perform a predefined operation corresponding to the location information of the user. For example, when it is identified that the user is present in an area set as a dangerous area based on the location information of the user, the processor 140 may output a message that the user is present in the area set as the dangerous area as a voice. However, this is merely an embodiment of the disclosure, and the predefined operation corresponding to the location information of the user may be variously set by the user.

When it is identified that the user is not present within the threshold distance of the electronic device 100, the processor 140 may control the communicator 130 to transmit a request signal requesting to perform an operation of obtaining the location information of the user to at least one external device. In other words, when the user is not present within the threshold distance of the electronic device 100 or it is difficult to determine whether the user is present within the threshold distance thereof, the processor 140 may control the communicator 130 to transmit the request signal requesting to perform the operation of obtaining the location information of the user with another external device to at least one external device.

The at least one external device which has received the request signal may obtain the location information of the user by using the feature information of a third signal (e.g., Wi-Fi signal) received from the other external device. The at least one external device which has obtained the location information of the user may perform the predefined operation corresponding to the location information of the user.

Meanwhile, when it is identified that the user does not carry the electronic device 100, the processor 140 may control the communicator 130 to transmit the request signal requesting to perform the operation of obtaining the location information of the user to at least one external device by using the second detecting method module 40. In other words, the processor 140 may not only obtain the location information of the user based on the signal received from the external device, but may also control the communicator 130 to transmit the request signal for controlling to perform the operation of obtaining the location information of the user to the external device.

After a preset period of time after transmitting the request signal to at least one external device, the processor 140 may control the communicator 130 to emit a fourth signal to the vicinity of the at least one external device via various paths. The fourth signal may be a Wi-Fi signal which may be transmitted/received via a Wi-Fi network.

A part or the entirety of the fourth signal emitted via the communicator 130 may be reflected by or transmitted through the user to be transmitted to the at least one external device. For example, the communicator 130 may emit the Wi-Fi signal via a plurality of paths under the control of the processor 140 and a part or the entirety of the emitted Wi-Fi signal may be reflected by or transmitted through the user located in the vicinity of the electronic device 100 to be transmitted to the at least one external device.

The at least one external device may obtain the location information of the user based on the feature information of the entirety or a part of the received fourth signal. The at least one external device may perform the operation corresponding to the obtained location information of the user. For example, if the external device is implemented as a smart lamp, when it is identified that the user is present within a threshold distance from the external device based on the obtained location information of the user, the external device may turn on a power of the lamp to light up an area around the user.

Meanwhile, the processor 140 may determine a detecting method for detecting the location of the user based on whether the battery of the electronic device 100 is being charged. The processor 140 may identify whether the battery is being charged via a wired charging cable or a wireless charger. The processor 140 may determine the detecting method based on a charging state of the battery using the second determination module 20.

When it is identified that the battery of the electronic device 100 is being charged, the processor 140 may determine the second detecting method by using the second determination module 20. In general, the state of the battery of the electronic device 100 which is being charged may imply that the user does not carry the electronic device. Accordingly, when the battery of the electronic device 100 is not being charged, the processor 140 may determine the first detecting method using the second determination module 20 and obtain the location information of the user using the first detecting method module 30 corresponding to the determined first detecting method.

When it is identified that the battery of the electronic device is being charged, the processor 140 may determine the second detecting method using the second determination module 20. The processor 140 may obtain the location information of the user using the second detecting method module 40 corresponding to the determined second detecting method.

In still another embodiment of the disclosure, when it is identified that the battery of the electronic device 100 is being charged, the processor 140 may obtain the location information of the electronic device using the feature information of the second signal received from at least one external device. The processor 140 may obtain the location information of the electronic device by inputting the feature information of the second signal received via the communicator 130 to the third location detecting model. For example, the processor 140 may obtain the location information of the electronic device 100 by inputting RSS information of the Wi-Fi signal received from the external device to the third location detecting model.

The processor 140 may identify whether the location of the electronic device 100 is a location where the location information of the user is able to be obtained using the second location detecting model based on the obtained location information of the electronic device 100.

The location where the location information of the user is able to be obtained using the second location detecting model may refer to a predefined location learned by the second location detecting model to output the location information of the user matched with a feature of an input signal. The predefined location learned by the second location detecting model may be variously determined by the user. The second location detecting model trained in advance may output the location information of the user matched with the feature information of the input second signal based on the predefined location that is learned.

The processor 140 may identify whether the current location of the electronic device is a location learned by the second location detecting model based on the obtained location information of the electronic device 100.

When it is identified that the location of the electronic device 100 is not the location learned by the second location detecting model, the processor 140 may determine the second detecting method among a plurality of detecting methods using the second determination module 20. When it is identified that the location of the electronic device is the location learned by the second location detecting model, the processor 140 may determine the first detecting method among the plurality of detecting methods using the second determination module 20. The processor 140 may obtain the location information of the user using the detecting method module corresponding to the determined detecting method.

In still another embodiment of the disclosure, the processor 140 may obtain first user location information using the first detecting method module 30 and obtain second user location information using the second detecting method module 40. In other words, the processor 140 may obtain the first and second user location information using the first detecting method and the second detecting method, respectively.

The processor 140 may identify whether a difference between the first user location information and the second user location information exceeds a threshold value. When it is identified that the difference between the first user location information and the second user location information exceeds the threshold value, the processor 140 may identify whether the user carries the electronic device.

When the difference between the user location information obtained using the first detecting method and the second detecting method, respectively is large, the processor 140 may identify whether the user carries the electronic device 100 to identify accurate information among the first and second user location information. The process of identifying whether the user carries the electronic device 100 has been described above, and therefore the overlapped description will not be repeated.

When it is identified that the user carries the electronic device 100, the processor 140 may determine the first user location information obtained using the first detecting method as final location information of the user. When the user carries the electronic device 100, the user location information obtained using the first detecting method may be comparatively accurate.

When it is identified that the user carries the electronic device 100, the processor 140 may determine the second user location information obtained using the second detecting method as the final location information of the user. When it is identified that the user does not carry the electronic device 100, the user location information obtained using the second detecting method may be comparatively accurate.

When it is identified that the difference between the first user location information and the second user location information does not exceed the threshold value, the processor 140 may determine the first user location information as the final location information of the user. When the user does not carry the electronic device 100, the difference between the first user location information and the second user location information may be highly likely to exceed the threshold value. Accordingly, when the difference between the first user location information and the second user location information is the threshold value or less, the processor 140 may identify that the user currently carries the electronic device and identify the first user location information as the final location information of the user.

The processor 140 may train the first location detecting model based on learning data obtained using dead reckoning from the first detecting method. Specifically, when it is identified that the battery of the electronic device 100 is being charged, the processor 140 may identify whether the location of the electronic device 100 is the location where the location information of the user is able to be obtained via the second location detecting model.

When it is identified that the location of the electronic device 100 is a location here the location information of the user is able to be obtained via the second location detecting model and it is identified that the user carries the electronic device 100 again which was being charged, the processor 140 may obtain movement information of the electronic device via the first sensor 110-1 based on the current location of the electronic device 100. For example, the processor 140 may obtain operation information of the user carrying the electronic device 100 or a movement direction by using the first sensor 110-1.

The processor 140 may identify a path that the user walked with the electronic device 100 based on the operation information of the user or movement direction. The processor 140 may match a specific location of the identified path with feature information of the Wi-Fi signal received from the AP. The processor 140 may generate a fingerprint for each specific location by using the feature information of the matched Wi-Fi signal for each specific location of the path. The processor 140 may add the generated fingerprint for each specific location to the fingerprint database. The processor 140 may train the first location detecting model using the updated fingerprint database as the learning data.

The function related to the artificial intelligence applied to an artificial neural network according to the disclosure is operated by the processor 140 and the memory 120. One or a plurality of processors 140 may perform control to process input data according to a predefined action rule stored in the memory 120 or an artificial intelligence model. In addition, if the one or the plurality of processors are artificial intelligence dedicated processors, the artificial intelligence dedicated processor may be designed to have a hardware structure specialized in processing of a specific artificial intelligence model.

The predefined action rule or the artificial intelligence model is formed through training. The forming through training herein may refer, for example, to forming a predefined action rule or an artificial intelligence model set to perform a desired feature (or object) by training a basic artificial intelligence model using a plurality of pieces of learning data by a learning algorithm Such training may be performed in a device demonstrating artificial intelligence according to the disclosure or performed by a separate server and/or system.

Examples of the learning algorithm include supervised learning, unsupervised learning, semi-supervised learning, or reinforcement learning, but is not limited to these examples.

The artificial intelligence model may include a plurality of artificial neural networks and the artificial neural network may include a plurality of layers. The plurality of neural network layers have a plurality of weight values, respectively, and execute neural network processing through a processing result of a previous layer and processing between the plurality of weights. The plurality of weights of the plurality of neural network layers may be optimized by the training result of the artificial intelligence model. For example, the plurality of weights may be updated to reduce or to minimize a loss value or a cost value obtained by the artificial intelligence model during the training process.

The artificial neural network may include convolutional neural network (CNN), deep neural network (DNN), recurrent neural network (RNN), restricted Boltzmann machine (RBM), deep belief network (DBN), bidirectional recurrent deep neural network (BRDNN), deep Q-network, and the like, but the artificial neural network of the disclosure is not limited to the above examples, unless otherwise noted.

Figure 2:
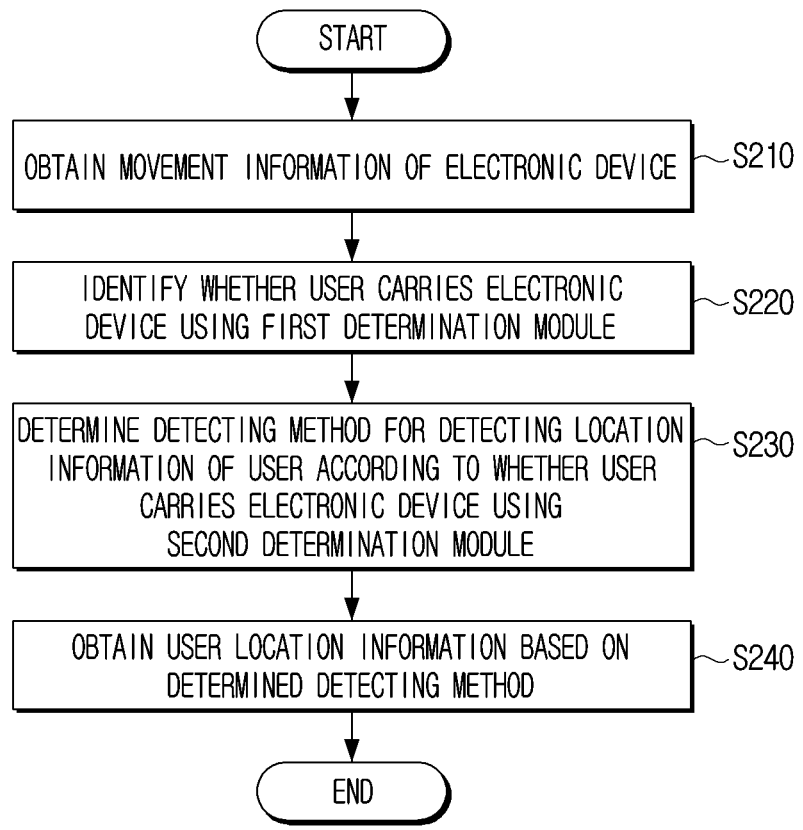
FIG. 2 is a flowchart for illustrating a method for controlling an electronic device according to an embodiment of the disclosure.

FIG. 2 is a flowchart for illustrating a method for controlling an electronic device according to an embodiment of the disclosure.

Referring to FIG. 2, the electronic device 100 may obtain movement information of the electronic device 100 in operation S210. The electronic device 100 may obtain the movement information of the electronic device 100 via a first sensor (e.g., a gyro sensor, an acceleration sensor, a geomagnetism sensor, and the like).

The electronic device 100 may identify whether the user carries the electronic device 100 using the first determination module in operation S220. The electronic device 100 may identify whether the user carries the electronic device 100 based on whether the movement information is changed within the threshold time.

For example, if the movement information is not changed within the threshold time, the electronic device 100 may identify that the user does not carry the electronic device 100 using the first determination module. If the movement information is changed within the threshold time, the electronic device 100 may identify that the user carries the electronic device 100 using the first determination module.

In another embodiment of the disclosure, the electronic device 100 may identify whether the user carries the electronic device 100 based on a biological signal of the user obtained via the second sensor 110-2. The embodiment related thereto has been described above, and therefore the overlapped description will not be repeated.

The electronic device 100 may determine a detecting method for detecting the location information of the user according to whether the user carries the electronic device using the second determination module in operation S230.

For example, when it is identified that the user carries the electronic device 100, the electronic device 100 may determine the first detecting method for obtaining the movement information of the electronic device 100 and the location information of the user using at least one of the feature information of the first signal received from the AP. The first detecting method has been described above, and therefore the overlapped description will not be repeated.

In still another embodiment of the disclosure, when it is identified that the user does not carry the electronic device 100, the electronic device 100 may determine the second determination method for obtaining the location information of the user using the feature information of the second signal received from at least one external device.

The electronic device 100 may obtain the user location information based on the determined detecting method in operation S240. The electronic device 100 may obtain the location information of the user using the detecting method module corresponding to the determined detecting method.

The embodiment in which the electronic device 100 obtains the location information of the user based on the second detecting method will be described with reference to FIG. 3. The embodiment in which, when the second determination method is determined, the electronic device 100 transmits a command for obtaining the location information of the user to the at least one external device will be described with reference to FIGS. 4 and 5.

Meanwhile, in still another embodiment of the disclosure, the electronic device 100 may determine the detecting method based on whether the battery is being charged. The embodiment related thereto will be described with reference to FIGS. 6 and 7.

Figure 3:
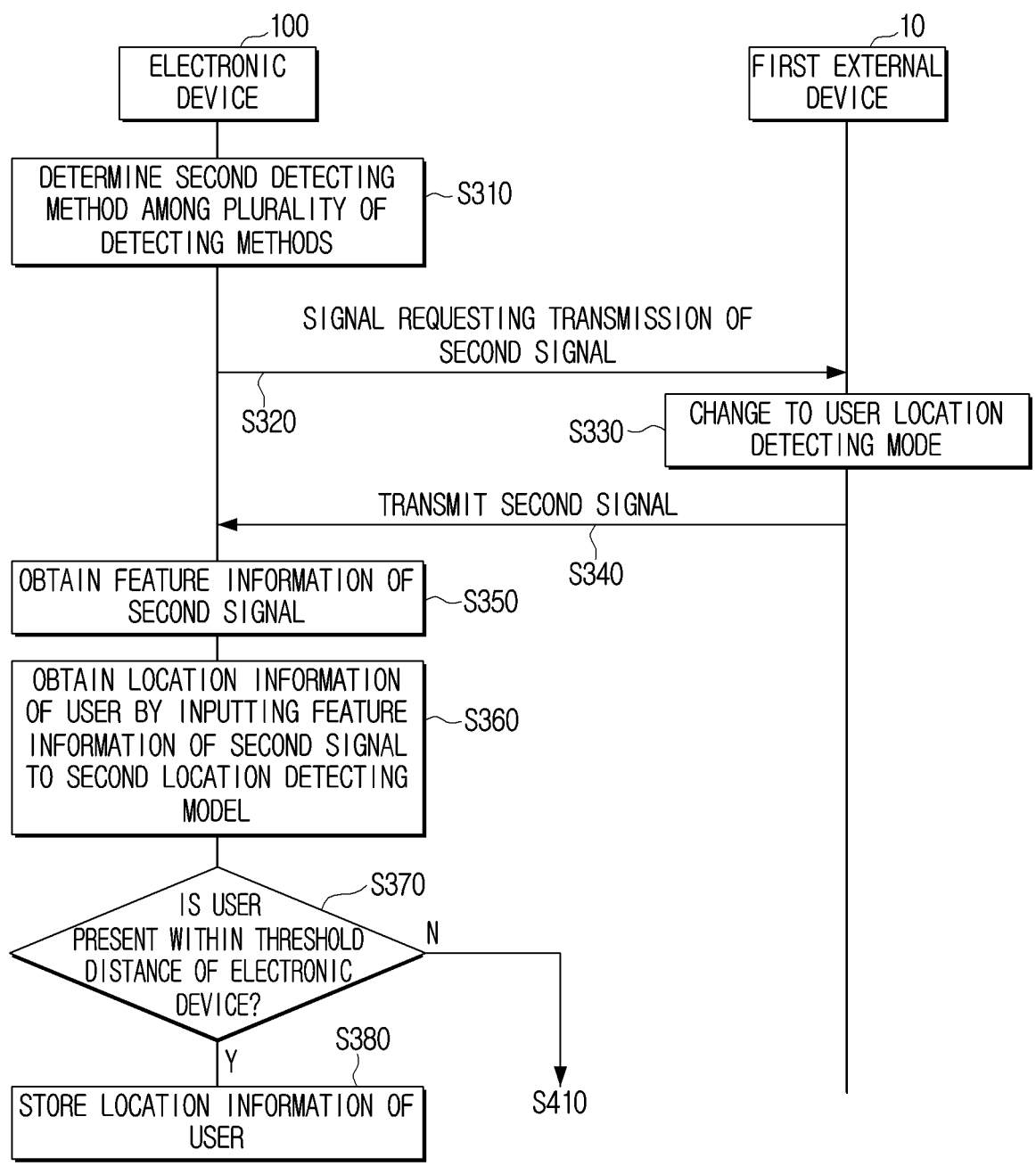
FIG. 3 is a flow diagram for illustrating operations between an electronic device and an external device according to an embodiment of the disclosure.

FIG. 3 is a flow diagram illustrating operations between an electronic device and an external device according to an embodiment of the disclosure.

Specifically, FIG. 3 is a flowchart for illustrating a process in which the electronic device 100 obtains the location information of the user using the second detecting method according to an embodiment of the disclosure. In other words, FIG. 3 is a flowchart for illustrating an operation after the electronic device 100 determines the second detecting method in operation S230 of FIG. 2.

Referring to FIG. 3, the electronic device 100 may determine the second detecting method among the plurality of detecting methods in operation S310. The electronic device 100 may transmit a signal for requesting transmission of the second signal for obtaining the location information of the user to a first external device 50 via the second detecting method module corresponding to the second detecting method in operation S320.

When the request signal is received, the first external device 50 may change a normal mode to a user location detecting mode in operation S330. The normal mode may refer to an operation mode in which operations corresponding to various commands input from the user may be performed. The user location detecting mode may refer to an operation mode for performing an operation of emitting various signals (e.g., Wi-Fi signal and the like) to a direction of another device so that the other device obtains the user location information or obtaining the location information of the user based on the feature information of the signal received from the other device.

While being operated in the user location detecting mode, the first external device 50 may emit the second signal to various paths to transmit a part or the entirety of the second signal to the electronic device 100 in operation S340. The second signal may be a Wi-Fi signal, but this is merely an embodiment and the second signal may include a Bluetooth signal and the like.

The electronic device 100 may receive a part or the entirety of the second signal emitted from the first external device 50 to obtain the feature information of the second signal in operation S350. The electronic device 100 may obtain the location information of the user by inputting the feature information of the second signal to the second location detecting model in operation S360. The location of the electronic device 100 may be one of a plurality of predefined locations learned by the second location detecting model.

For example, the electronic device 100 may obtain the location information of the user for estimating the location of the user based on the predefined location of the electronic device 100 by inputting the CSI magnitude change amount of the Wi-Fi signal received from the first external device 50 via the first path and the second path to the second location detecting model via the second detecting method module 40.

The electronic device 100 may identify whether the user is present within the threshold distance of the electronic device 100 based on the obtained location information of the user in operation S370. When it is identified that the user is present within the threshold distance, the electronic device 100 may store the obtained location information of the user in operation S380.

The electronic device 100 may perform a predefined operation corresponding to the location information of the user. For example, when it is identified that the user is present in an area set as a dangerous area based on the location information of the user, the electronic device 100 may output a message that the user is present in the area set as the dangerous area as a voice. However, this is merely an embodiment of the disclosure, and the predefined operation corresponding to the location information of the user may be variously set by the user.

The operation performed by the electronic device 100 when it is identified that the user is not present within the threshold distance of the electronic device 100 will be described with reference to FIG. 4.

Figure 4:
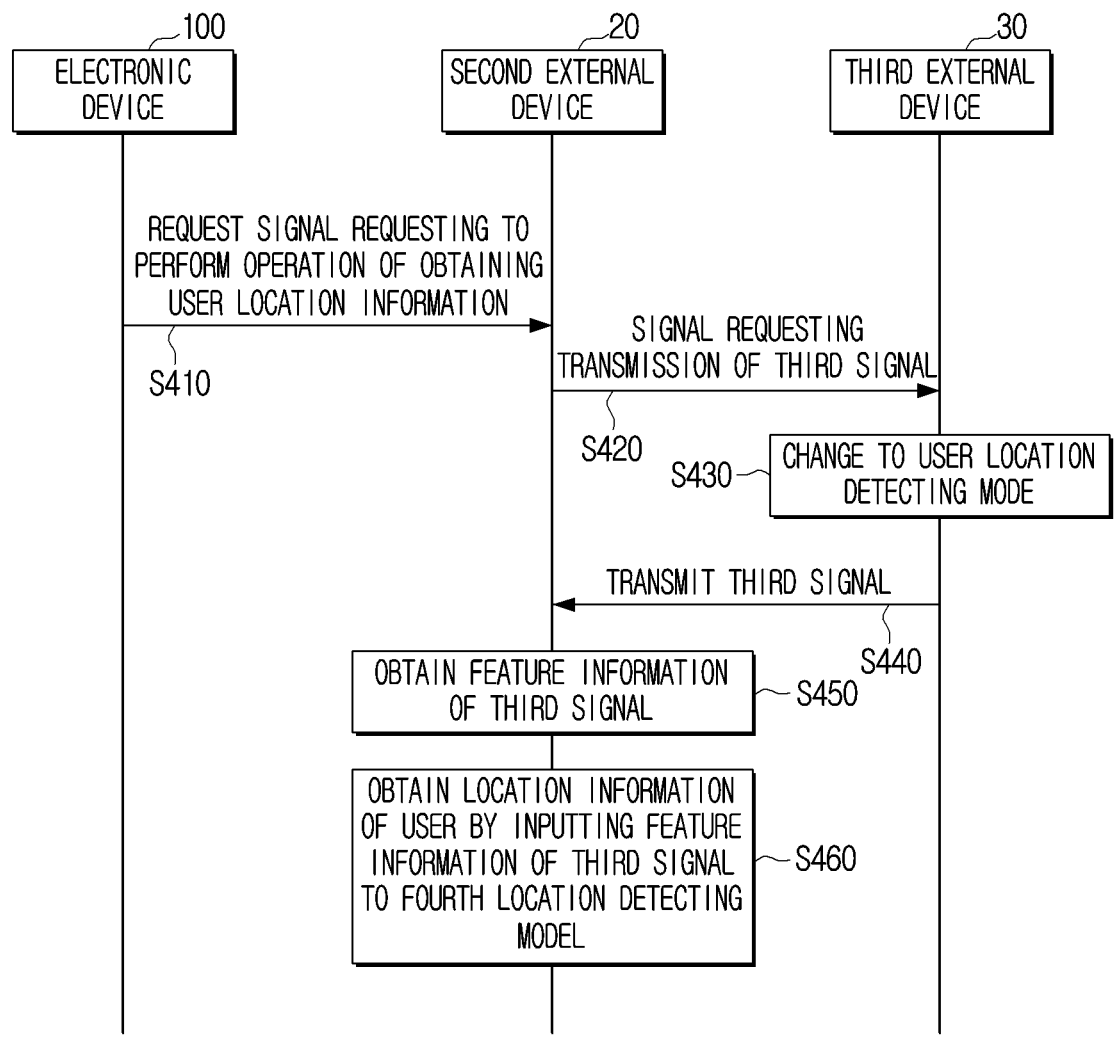
FIG. 4 is a flow diagram for illustrating operations between an electronic device and a plurality of external devices according to an embodiment of the disclosure.

FIG. 4 is a flow diagram for illustrating operations between an electronic device and a plurality of external devices according to an embodiment of the disclosure.

Specifically, FIG. 4 is a flowchart for illustrating the operation performed by the electronic device 100 when it is identified that the user is not present within the threshold distance according to an embodiment of the disclosure.

When it is identified that the user is not present within the threshold distance of the electronic device 100 based on the location information of the user, the electronic device 100 may transmit a request signal for requesting to perform the operation of obtaining the location information of the user to the at least one external device.

Referring to FIG. 4, the electronic device 100 may transmit the request signal for requesting to perform the operation of obtaining the location information of the user to a second external device 60 in operation S410. In an embodiment of the disclosure, the second external device 60 may be the same or different from the first external device 50.

When the request signal is received, the second external device 60 may transmit a signal for requesting a third external device 70 to transmit a third signal for obtaining the location information of the user to the third external device 70 in operation S420. When the signal for requesting to transmit the third signal is received, the third external device 70 may change the normal mode to the user location detecting mode in operation S430.

While being operated in the user location detecting mode, the third external device 70 may emit the third signal in various paths so that a part or the entirety of the third signal is transmitted to the second external device 60 in operation S440. The third signal may be a Wi-Fi signal but this is merely an embodiment of the disclosure, and the third signal may include a Bluetooth signal and the like.

The second external device 60 may receive a part or the entirety of the third signal emitted from the third external device 70 to obtain the feature information of the third signal in operation S450. The second external device 60 may obtain the location information of the user by inputting the feature information of the third signal to a fourth location detecting model in operation S460. The fourth location detecting model may be an artificial intelligence model for performing the same operation as the second location detecting model.

For example, the second external device 60 may obtain the location information of the user for estimating the location of the user based on a predefined location of the second external device 60 by inputting the CSI magnitude change amount of the Wi-Fi signal received from the third external device 70 via a third path and a fourth path to a fifth location detecting model.

Figure 5:
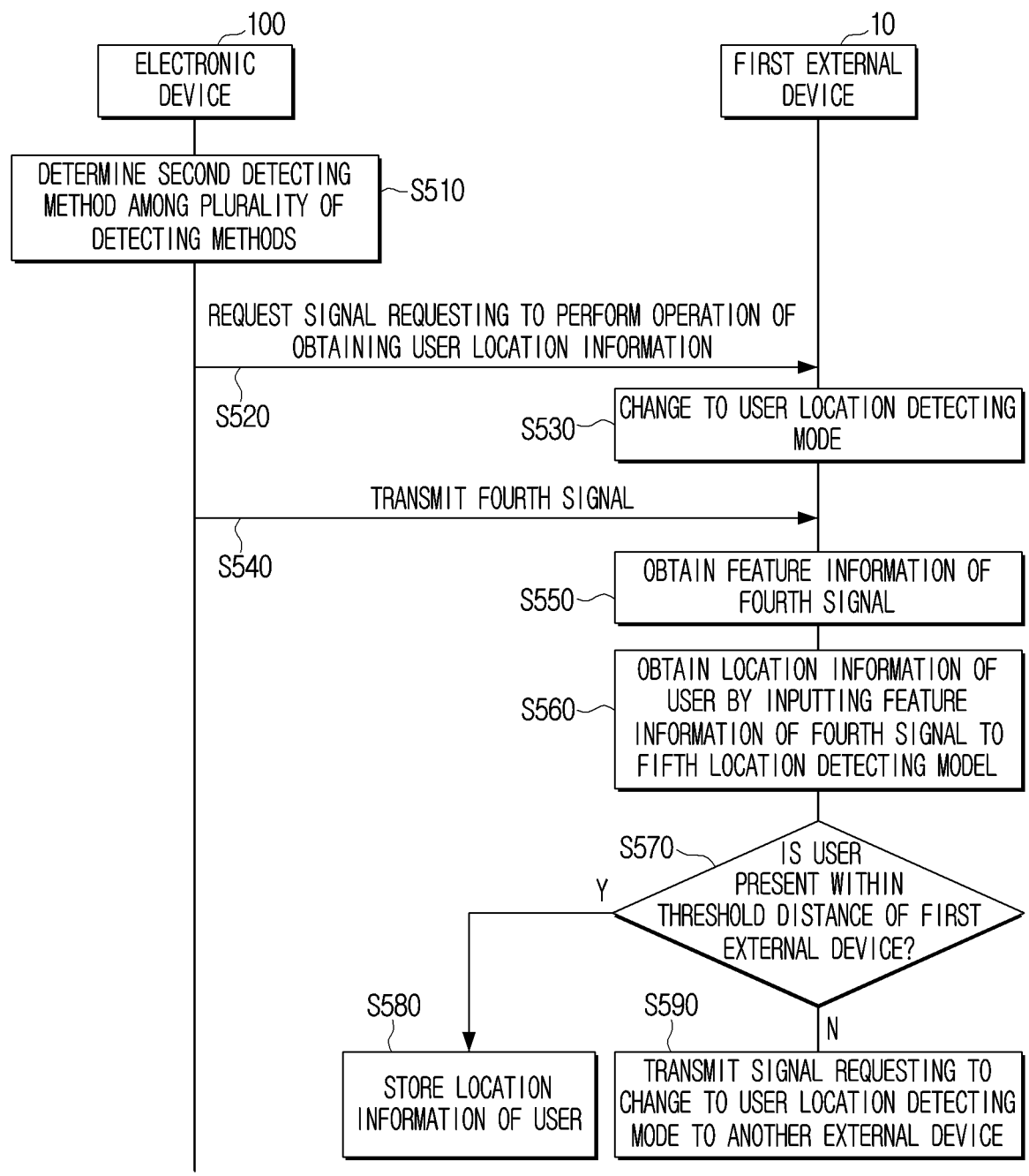
FIG. 5 is a flow diagram for illustrating operations between an electronic device and an external device according to an embodiment.

FIG. 5 is a flow diagram for illustrating operations between an electronic device and an external device according to an embodiment.

Specifically, FIG. 5 is a flowchart for illustrating an operation in which the first external device 50 obtains the location information of the user by the electronic device 100 according to an embodiment of the disclosure. Referring to FIG. 5, it is a flowchart for illustrating an operation after the electronic device 100 determines the second detecting method in S230 of FIG. 2.

The electronic device 100 may determine the second detecting method among the plurality of detecting methods in operation S510. The electronic device 100 may transmit a request signal for requesting to perform the operation of obtaining the location information of the user to the first external device 50 by using the second detecting method module corresponding to the second detecting method in operation S520.

When the request signal for requesting to perform the operation of obtaining the location information of the user is received, the first external device 50 may change the normal mode to the user location detecting mode in operation S530.

After a preset period of time after transmitting the request signal, the electronic device 100 may emit a fourth signal in various paths so that a part or the entirety of the fourth signal is transmitted to the second external device 60 in operation S540. Herein, the fourth signal may be a Wi-Fi signal, but this is merely an embodiment and the fourth signal may include a Bluetooth signal and the like.

However, this is merely an embodiment of the disclosure, and when the normal mode is changed to the user location detecting mode, the first external device 50 may transmit a signal indicating that the operation mode has changed to the electronic device 100. When the signal indicating that the operation mode has changed is received, the electronic device 100 may emit the fourth signal so that a part or the entirety of the fourth signal is transmitted to the second external device 60.

The first external device 50 may receive a part or the entirety of the fourth signal emitted from the electronic device 100 to obtain the feature information of the fourth signal in operation S550. The second external device 60 may obtain the location information of the user by inputting the feature information of the third signal to the fourth location detecting model in operation S560. The fourth location detecting model may be an artificial intelligence model for performing the same operation as the second or third location detecting model.

For example, the first external device 50 may obtain the location information of the user for estimating the location of the user based on the predefined location of the first external device 50 by inputting the CSI magnitude change amount of the Wi-Fi signal received from a fourth external device 80 via a fifth path and a sixth path to the fifth location detecting model.

The first external device 50 may identify whether the user is present within the threshold distance of the first external device based on the location information of the user in operation S570. When it is identified that the user is present within the threshold distance of the first external device 10, the first external device 50 may store the obtained location information of the user in operation S580.

The first external device 50 may perform the predefined operation corresponding to the location information of the user. For example, when the first external device 50 is implemented as a refrigerator and it is identified that the user is within a preset distance of the refrigerator based on the location information of the user, the first external device 50 may display a UI showing information regarding thins in the refrigerator. However, this is merely an embodiment of the disclosure, and the predefined operation corresponding to the location information of the user may be variously set by the user.

When it is identified that the user is not present within the threshold distance of the first external device 50, the first external device 50 may transmit a signal for requesting the change to the user location detecting mode to the other external device in operation S590. In other words, when the location of the user is not detected, the first external device 50 may transmit a request signal for requesting to detect the location of the user to the other device. The other device which has received the request signal may perform the operation for obtaining the location information of the user by changing the mode to the user location detecting mode.

Figure 6:
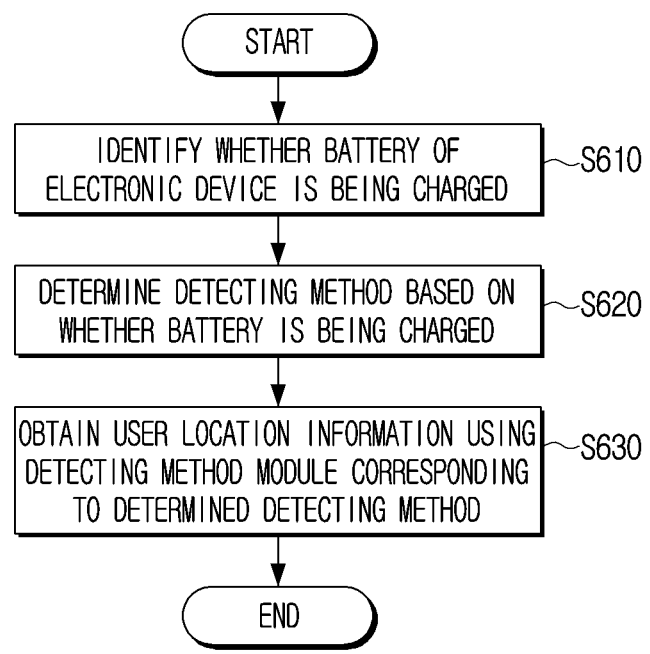
FIG. 6 is a flowchart for illustrating a process of determining a detecting method based on whether a battery of an electronic device is being charged according to an embodiment of the disclosure.

FIG. 6 is a flowchart for illustrating a process of determining a detecting method based on whether a battery of an electronic device is being charged according to an embodiment of the disclosure.

Specifically, FIG. 6 is a flowchart for illustrating a process in which the electronic device 100 determines the detecting method based on whether the battery is being charged according to an embodiment of the disclosure.

Referring to FIG. 6, the electronic device 100 may identify whether the battery is being charged in operation S610. The electronic device 100 may identify whether the battery is currently being charged through a wired cable connected to a device supplying power or a wireless charging method.

The electronic device 100 may determine the user detecting method based on whether the battery is being charged in operation S620. The battery being charged may imply that the user is highly likely to not carry the electronic device. When it is identified that the battery of the electronic device 100 is being charged, the electronic device 100 may determine the second detecting method.

The battery not being charged may imply that the user is highly likely to carry and use the electronic device 100. When it is identified that the battery of the electronic device 100 is not being charged, the electronic device 100 may determine the first detecting method.

The electronic device 100 may obtain the user location information using the detecting method module corresponding to the determined detecting method in operation S630. The process of obtaining the location information of the user using each detecting method module has been described above, and therefore the overlapped description will not be repeated.

Figure 7:
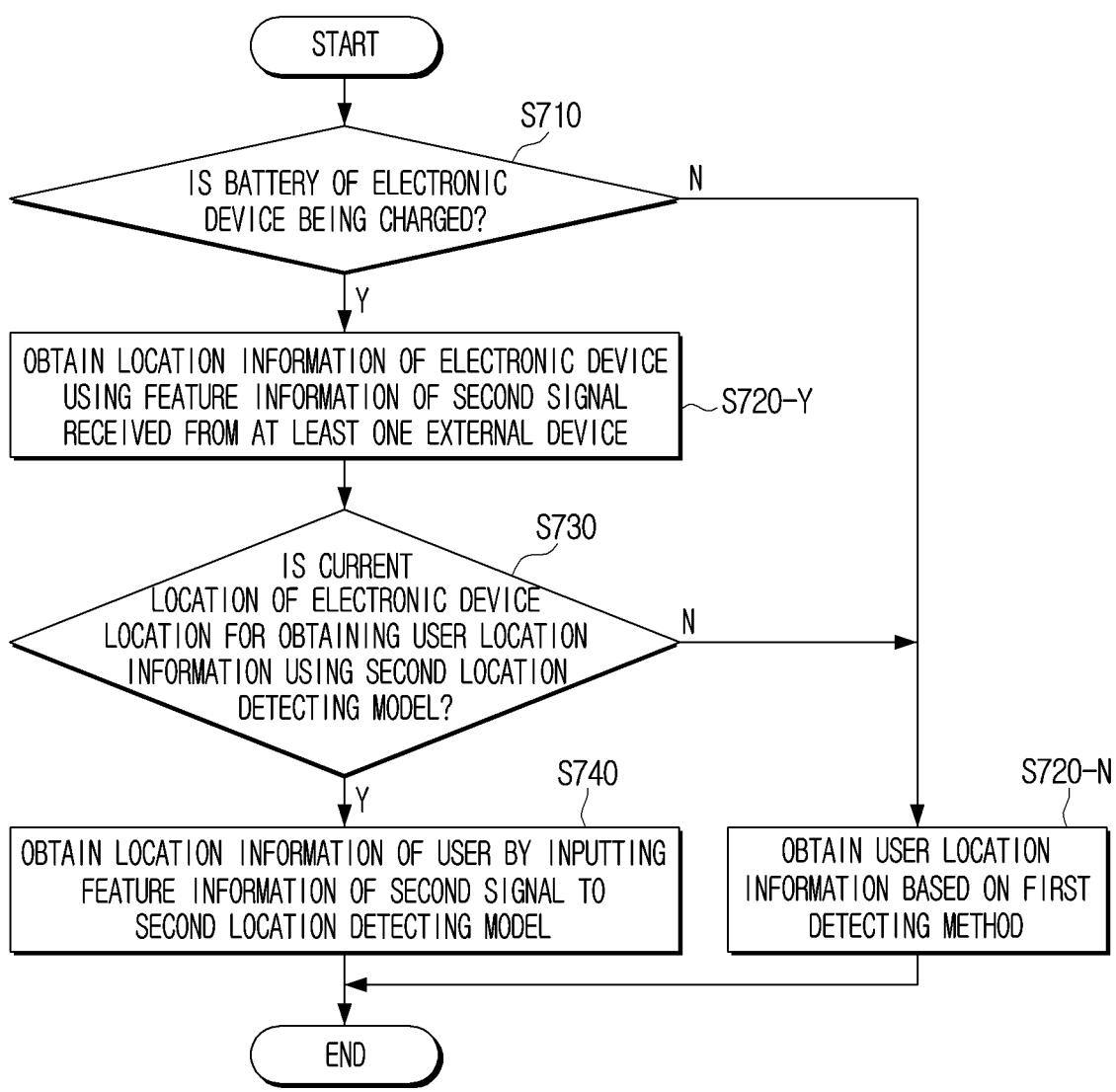
FIG. 7 is a flowchart for illustrating a process for determining a detecting method based on whether a battery of an electronic device is being charged and a location of the electronic device according to an embodiment of the disclosure.

FIG. 7 is a flowchart for illustrating a process for determining a detecting method based on whether a battery of an electronic device is being charged and a location of the electronic device according to an embodiment of the disclosure.

Specifically, FIG. 7 is a flowchart for illustrating a method for obtaining the user location information by the electronic device 100 based on whether the battery is being charged according to an embodiment of the disclosure.

Referring to FIG. 7, the electronic device 100 may identify whether the battery of the electronic device 100 is being charged in operation S710. When it is identified that the battery is being charged, the electronic device 100 may obtain current location information of the electronic device 100 using the feature information of the second signal received from the at least one external device in operation S720-Y.

The electronic device 100 may obtain the location information of the electronic device by inputting the feature information of the second signal received from the at least one external device to the third location detecting model. For example, the electronic device 100 may obtain the location information of the electronic device 100 by inputting the RSS information of the Wi-Fi signal received from the at least one external device to the third location detecting model.

The electronic device 100 may identify whether the current location of the electronic device 100 is a location for obtaining the user location information using the second location detecting model based on the location information of the electronic device 100 in operation S730.

The second location detecting model may be trained using the feature information of the second signal received from the external device at a plurality of predefined locations determined by the user and the location information of the user matched with the feature information of the second signal. The location for obtaining the user location information using the second location detecting model may refer to a predefined location learned by the second location detecting model.

When it is identified that the current location of the electronic device is a location for obtaining the user location information using the second location detecting model, the electronic device 100 may obtain the location information of the user by inputting the feature information of the second signal to the second location model in operation S740.

When it is not identified that the current location of the electronic device is a location for obtaining the user location information using the second location detecting model, the electronic device 100 may obtain the user location information based on the first detecting method in operation S720-N.

Meanwhile, when it is identified that the battery is not being charged, the electronic device 100 may obtain the user location information based on the first detecting method in operation S720-N.

Figure 8:
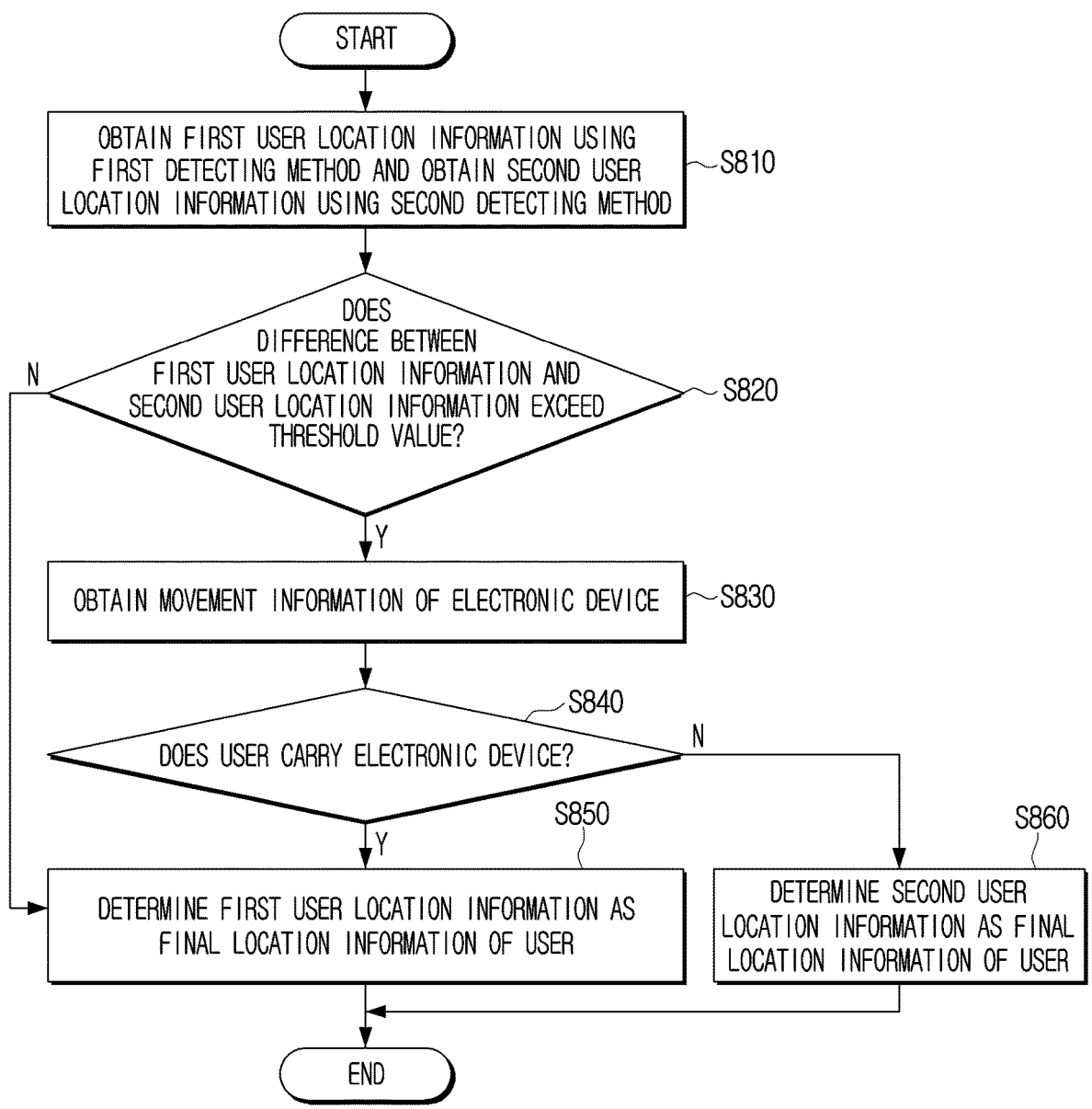
FIG. 8 is a flowchart for illustrating a process in which an electronic device obtains final location information of a user according to an embodiment of the disclosure.

FIG. 8 is a flowchart for illustrating a process in which an electronic device obtains final location information of a user according to an embodiment of the disclosure.

Referring to FIG. 8, the electronic device 100 may obtain the first user location information using the first detecting method and the second user location information using the second detecting method in operation S810.

The electronic device 100 may obtain the first user location information using the fingerprint comparing method or dead reckoning from the first detecting method. At the same time or regardless of the order, the electronic device 100 may obtain the location information of the user based on the feature information of the second signal received from the at least one external device.

The electronic device 100 may identify whether the difference between the first user location information and the second user location information exceeds the threshold value in operation S820. If the difference between the first user location information and the second user location information obtained using the first detecting method and the second detecting method, respectively is large, the electronic device 100 may identify whether the user currently carries the electronic device 100 to identify accurate information among the first and second user location information.

Accordingly, the electronic device 100 may obtain the movement information of the electronic device 100 in operation S830. The electronic device 100 may identify whether the user carries (have) the electronic device 100 based on the obtained movement information in operation S840. However, this is merely an embodiment of the disclosure, and the electronic device 100 may identify whether the user carries the electronic device 100 based on the biological signal of the user obtained via the second sensor.

When it is identified that the user carries the electronic device 100, the electronic device 100 may determine the first user location information as the final location information of the user in operation S850. The first detecting method is a method for detecting the location of the user assuming that the user carries the electronic device 100. Accordingly, when the user carries the electronic device 100, the first user location information obtained using the first detecting method may be comparatively accurate.

When it is identified that the user does not carry the electronic device 100, the electronic device 100 may determine the second user location information as the final location information of the user in operation S860. The second detecting method is a method for detecting the location of the user assuming that the user does not carry the electronic device 100. Accordingly, when the user does not carry the electronic device 100, the second user location information obtained using the second detecting method may be comparatively accurate.

Meanwhile, when it is identified that the difference between the first user location information and the second user location information does not exceed the threshold value, the electronic device 100 may determine the first user location information as the final location information of the user in operation S850.

When the user does not carry the electronic device 100, the difference between the first user location information and the second user location information may be highly likely to exceed the threshold value. Accordingly, when the difference between the first user location information and the second user location information is threshold value or less, the electronic device 100 may identify that the user currently carries the electronic device and identify the first user location information as the final location information of the user.

Figure 9:
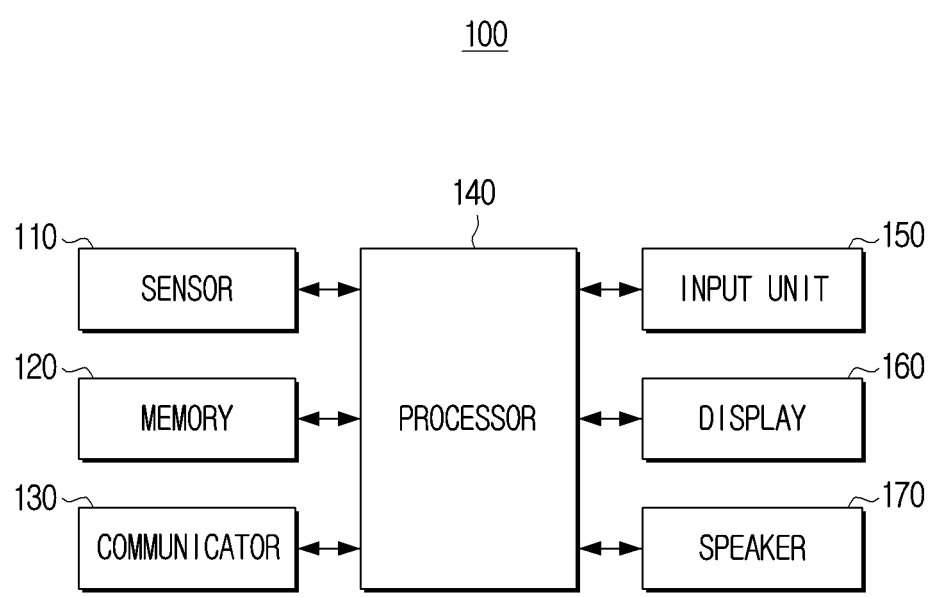
FIG. 9 is a block diagram for specifically illustrating a configuration of an electronic device according to an embodiment of the disclosure.

FIG. 9 is a block diagram for specifically illustrating a configuration of an electronic device according to an embodiment of the disclosure.

Referring to FIG. 9, the electronic device 100 may include the sensor 110, the memory 120, the communicator 130, the processor 140, an input unit 150, a display 160, and a speaker 170. The sensor 110, the memory 120, the communicator 130, and the processor 140 have been described above with reference to FIG. 1, and therefore the overlapped description will not be repeated.

The input unit 150 may receive a user input for controlling the electronic device 100. More particularly, the input unit 150 may include a touch panel for receiving a user touch using user's fingers or a stylus pen, a button for receiving user manipulation, and the like. In addition, the input unit 150 may be implemented as other input devices (e.g., a keyboard, a mouse, a motion input unit, and the like). More particularly, the input unit 150 may receive a user command for changing the threshold value described above with reference to FIG. 8.

In addition, the input unit 150 may receive a user command for setting an operation corresponding to the location information of the user. When the user command for setting the operation corresponding to the location information of the user is received via the input unit 150, the processor 140 may store the operation corresponding to the location of the user in the memory 120 based on the received user command.

The display 160 may display various pieces of information according to the control of the processor 140. The display 160 may be implemented as a touch screen with the touch panel or may be implemented as a flexible display and the like.

The display 160 may display a UI screen including the location information of the user under the control of the processor 140. The UI screen may include information regarding a method for obtaining the location information of the user by the processor 140. In addition, the UI screen may include information regarding an operation to be performed corresponding to the current location of the user and a UI for changing or adding the operation to be performed.

When the user is not present within the threshold distance of the electronic device 100, the display 160 may display a message or an indicator indicating that the user is not present within the threshold distance of the electronic device 100 under the control of the processor 140.

According to the various embodiments of the disclosure, the electronic device may detect the location of the user by the optimized method according to whether the user carries the electronic device. Therefore, the user may receive accurate location determination information indoors.

Meanwhile, it should be noted that the accompanying drawings in the disclosure are not for limiting the technologies disclosed in this disclosure to a specific embodiment of the disclosure, but they should be interpreted to include all modifications, equivalents and/or alternatives of the embodiments of the disclosure. In relation to explanation of the drawings, similar reference numerals may be used for similar elements.

In this disclosure, the terms, such as "comprise", "may comprise", "consist of", or "may consist of" are used herein to designate a presence of corresponding features (e.g., constituent elements, such as number, function, operation, or part), and not to preclude a presence of additional features.

In this disclosure, expressions, such as "A or B", "at least one of A [and/or] B,", or "one or more of A [and/or] B," include all possible combinations of the listed items. For example, "A or B", "at least one of A and B,", or "at least one of A or B" includes any of (1) at least one A, (2) at least one B, or (3) at least one A and at least one B.

The expressions "first," "second" and the like used in the disclosure may denote various elements, regardless of order and/or importance, and may be used to distinguish one element from another, and does not limit the elements.

If it is described that a certain element (e.g., a first element) is "operatively or communicatively coupled with/ to" or is "connected to" another element (e.g., a second element), it should be understood that the certain element may be connected to the other element directly or through still another element (e.g., a third element). On the other hand, if it is described that a certain element (e.g., the first element) is "directly coupled to" or "directly connected to" another element (e.g., the second element), it may be understood that there is no element (e.g., the third element) between the certain element and the another element.

In addition, the expression "configured to" used in the disclosure may be interchangeably used with other expressions, such as "suitable for," "having the capacity to," "designed to," "adapted to," "made to," and "capable of," depending on cases. Meanwhile, the expression "configured to" does not necessarily refer to a device being "specifically designed to" in terms of hardware. Instead, under some circumstances, the expression "a device configured to" may refer to the device being "capable of" performing an operation together with another device or component. For example, the phrase "a unit or a processor configured (or set) to perform A, B, and C" may refer, for example, and without limitation, to a dedicated processor (e.g., an embedded processor) for performing the corresponding operations, a generic-purpose processor (e.g., a central processing unit (CPU) or an application processor), or the like, that can perform the corresponding operations by executing one or more software programs stored in a memory device.

An electronic device according to various embodiments of the disclosure may include at least one of, for example, a smartphone, a tablet PC, a desktop PC, a laptop PC, a netbook PC, a server, a PDA, a medical device, or a wearable device. In addition, in some embodiments of the disclosure, the external device may include at least one of, for example, a television, a refrigerator, an air conditioner, an air purifier, a set-top box, and a media box (e.g., SAMSUNG HOMESYNC™, APPLE TV™, or GOOGLE TV™).

Various embodiments of the disclosure may be implemented as software including instructions stored in machine (e.g., computer)-readable storage media. The machine is a device which invokes instructions stored in the storage medium and is operated according to the invoked instructions, and may include a server cloud according to the embodiments described above. In a case where the instruction is executed by a processor, the processor may perform a function corresponding to the instruction directly or using other elements under the control of the processor. The instruction may include a code made by a compiler or a code executable by an interpreter. The machine-readable storage medium may be provided in a form of a non-transitory storage medium. Here, the "non-transitory storage medium" is tangible and may not include signals, and it does not distinguish that data is semi-permanently or temporarily stored in the storage medium. For example, the "non-transitory storage medium" may include a buffer temporarily storing data.

According to an embodiment of the disclosure, the methods according to various embodiments disclosed in this disclosure may be provided to be included in a computer program product. The computer program product may be exchanged between a seller and a purchaser as a commercially available product. The computer program product may be distributed in the form of a machine-readable storage medium (e.g., compact disc read only memory (CD-ROM)) or distributed online through an application store (e.g., PlayStore™). In a case of the on-line distribution, at least a part of the computer program product may be at least temporarily stored or temporarily generated in a storage medium, such as a memory of a server of a manufacturer, a server of an application store, or a relay server.

Each of the elements (e.g., a module or a program) according to various embodiments described above may include a single entity or a plurality of entities, and some sub-elements of the abovementioned sub-elements may be omitted or other sub-elements may be further included in various embodiments. Alternatively or additionally, some elements (e.g., modules or programs) may be integrated into one entity to perform the same or similar functions performed by each respective element prior to the integration. Operations performed by a module, a program, or other elements, in accordance with various embodiments of the disclosure, may be performed sequentially, in a parallel, repetitive, or heuristically manner, or at least some operations may be performed in a different order, omitted, or may add a different operation.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
   a communicator comprising circuitry;
   a first sensor configured to detect movement information of the electronic device;
   a memory comprising:
      a first determination module configured to determine whether a user carries the electronic device, and
      a second determination module configured to determine a detecting method for detecting a user location; and
   a processor configured to:
      identify whether a user of the electronic device carries the electronic device based on the movement information of the electronic device obtained by the first sensor by using the first determination module,
      determine a detecting method for detecting location information of the user according to whether the user carries the electronic device by using the second determination module,
      based on the user being identified to carry the electronic device, determine a first detecting method for obtaining the location information of the user using at least one of the movement information of the electronic device or feature information of a first signal received from an access point (AP) via the communicator; and
      based on the user being identified to not carry the electronic device, determine a second detecting method for obtaining the location information of the user using feature information of a second signal received from at least one external device via the communicator.

2. The electronic device of claim 1, wherein the processor is further configured to:
   based on the movement information being not changed within threshold time, identify that the user does not carry the electronic device by using the first determination module, and
   based on the movement information being changed within the threshold time, identify that the user carries the electronic device by using the first determination module.

3. The electronic device of claim 1, further comprising:
   a second sensor configured to detect a biological signal of the user by coming into contact with the user of the electronic device,
   wherein the processor is further configured to identify whether the user of the electronic device carries the electronic device based on whether the biological signal of the user is able to be detected via the second sensor, by using the first determination module.

4. The electronic device of claim 1, wherein the processor is further configured to:
   based on the second detecting method being determined, control the communicator to transmit a signal requesting transmission of the second signal for obtaining the location information of the user to the at least one external device by using the second detecting method module; and
   based on the feature information of the second signal being obtained by receiving the second signal from the at least one external device via the communicator, obtain the location information of the user by inputting the feature information of the second signal to a location detecting model.

5. The electronic device of claim 1,
   wherein the processor is further configured to, based on the second detecting method being determined, control the communicator to transmit a request signal requesting to perform an operation of obtaining the location information of the user to the at least one external device, and
   wherein the at least one external device, which has received the request signal, is configured to obtain the location information of the user based on feature information of a third signal received from another external device.

6. The electronic device of claim 4,
   wherein the processor is further configured to, based on the user being identified to be not present within a threshold distance from the electronic device based on the feature information of the second signal, control the communicator to transmit a request signal requesting to perform an operation of obtaining the location information of the user to the at least one external device, and
   wherein the at least one external device, which has received the request signal, is configured to obtain the location information of the user based on the feature information of the third signal received from another external device.

7. The electronic device of claim 1, wherein the processor is further configured to:
   identify whether a battery of the electronic device is being charged,
   determine the detecting method for detecting the location information of the user according to whether the battery of the electronic device is being charged by using the second determination module,
   based on the battery of the electronic device being identified as being charged, determine the second detecting method, and
   based on the battery of the electronic device being identified as not being charged, determine the first detecting method.

8. The electronic device of claim 1, wherein the processor is further configured to:
   based on a battery of the electronic device being identified as being charged, identify a location of the electronic device by using the second signal received from the at least one external device, and
   identify whether the location of the electronic device is a location for obtaining the location information of the user via a location detecting model.

9. The electronic device of claim 8, wherein the processor is further configured to:
   based on the location of the electronic device being identified as the location for obtaining the location information of the user via the location detecting model, obtain the location information of the user by the second detecting method, and
   based on the location of the electronic device being not identified as the location for obtaining the location information of the user via the location detecting model, obtain the location information of the user by using the first detecting method.

10. The electronic device of claim 8, wherein the processor is further configured to:
based on the user being identified to carry the electronic device after the location of the electronic device is identified as the location for obtaining the location information of the user via the location detecting model, obtain movement information of the electronic device via the first sensor based on the location of the electronic device, and
train the location detecting model based on the movement information of the electronic device and feature information of a third signal received from the AP via the communicator.

11. A method for controlling an electronic device including a first sensor configured to detect movement information of the electronic device, a first determination module configured to determine whether a user carries the electronic device, and a second determination module configured to determine a detecting method for detecting a user location, the method comprising:
identifying whether a user of the electronic device carries the electronic device based on the movement information of the electronic device obtained by the first sensor by using the first determination module; and
determining a detecting method for detecting location information of the user according to whether the user carries the electronic device by using the second determination module,
wherein the determining of the detecting method comprises:
based on the user being identified to carry the electronic device, determining a first detecting method for obtaining the location information of the user using at least one of the movement information of the electronic device or feature information of a first signal received from an AP, and
based on the user being identified to not carry the electronic device, determining a second detecting method for obtaining the location information of the user using feature information of a second signal received from at least one external device.

12. The method of claim 11, wherein the identifying comprises:
based on the movement information being not changed within threshold time, identifying that the user does not carry the electronic device by using the first determination module; and
based on the movement information being changed within the threshold time, identifying that the user carries the electronic device by using the first determination module.

13. The method of claim 1, wherein the identifying comprises identifying whether the user of the electronic device carries the electronic device based on whether a biological signal of the user is able to be detected via a second sensor configured to detect the biological signal of the user, by using the first determination module.

14. The method of claim 11, further comprising:
based on the second detecting method being determined, transmitting a signal requesting transmission of the second signal for obtaining the location information of the user to the at least one external device by using the second detecting method module; and
based on the feature information of the second signal being obtained by receiving the second signal from the at least one external device, obtaining the location information of the user by inputting the feature information of the second signal to a location detecting model.

15. The method of claim 11, further comprising:
based on the second detecting method being determined, transmitting a request signal requesting to perform an operation of obtaining the location information of the user to the at least one external device,
wherein the at least one external device which has received the request signal is configured to obtain the location information of the user based on feature information of a third signal received from another external device.

16. The method of claim 14, further comprising:
based on the user being identified to be not present within a threshold distance from the electronic device based on the feature information of the second signal, transmitting a request signal requesting to perform an operation of obtaining the location information of the user to the at least one external device,
wherein the at least one external device which has received the request signal is configured to obtain the location information of the user based on the feature information of the third signal received from another external device.

17. The method of claim 11, wherein the identifying comprises:
identifying whether a battery of the electronic device is being charged;
determining the detecting method for detecting the location information of the user according to whether the battery of the electronic device is being charged by using the second determination module;
based on the battery of the electronic device being identified as being charged, determining the second detecting method; and
based on the battery of the electronic device being identified as not being charged, determining the first detecting method.

18. The method of claim 11, further comprising:
based on a battery of the electronic device being identified as being charged, identifying a location of the electronic device by using the second signal received from the at least one external device; and
identifying whether the location of the electronic device is a location for obtaining the location information of the user via a location detecting model.

19. The method of claim 18, wherein the identifying of whether the location of the electronic device is the location for obtaining the location information of the user via the location detecting model comprises:
based on the location of the electronic device being identified as the location for obtaining the location information of the user via the location detecting model, obtaining the location information of the user by the second detecting method; and
based on the location of the electronic device being not identified as the location for obtaining the location information of the user via the location detecting model, obtaining the location information of the user by using the first detecting method.

20. The method of claim 18, further comprising:
based on the user being identified to carry the electronic device after the location of the electronic device is identified as the location for obtaining the location information of the user via the location detecting model, obtaining movement information of the electronic device via the first sensor based on the location of the electronic device; and training the location detecting model based on the movement information of the electronic device and feature information of a third signal received from the AP.

* * * * *